US008175890B2

(12) United States Patent (10) Patent No.: US 8,175,890 B2
Whittacre et al. (45) Date of Patent: May 8, 2012

(54) PHARMACY BASED METHOD AND ALGORITHM FOR HANDLING OF RADIOACTIVE PHARMACEUTICALS AND GENERATING OF REPORTS THEREFROM

(75) Inventors: Bretten Whittacre, Henderson, NV (US); Jared Johnson, Henderson, NV (US); Troy Curnutt, Pocatello, ID (US)

(73) Assignee: Biodose, LLC, Las Vegas, NV (US)

( * ) Notice: Subject to any disclaimer, the term of this patent is extended or adjusted under 35 U.S.C. 154(b) by 2422 days.

(21) Appl. No.: 10/447,727

(22) Filed: May 28, 2003

(65) Prior Publication Data

US 2005/0101822 A1 May 12, 2005
US 2009/0023974 A9 Jan. 22, 2009

Related U.S. Application Data

(63) Continuation-in-part of application No. 10/283,480, filed on Oct. 29, 2002, now Pat. No. 7,630,907.

(60) Provisional application No. 60/384,501, filed on May 29, 2002, provisional application No. 60/335,088, filed on Oct. 30, 2001.

(51) Int. Cl.
*G06Q 10/00* (2012.01)
*G06Q 50/00* (2012.01)
(52) U.S. Cl. ............................................... 705/2; 705/3
(58) Field of Classification Search .................. 705/2–3; 704/275
See application file for complete search history.

(56) References Cited

U.S. PATENT DOCUMENTS

| | | | |
|---|---|---|---|
| 5,479,969 A * | 1/1996 | Hardie et al. ................. 141/130 |
| 5,664,112 A | 9/1997 | Sturgeon et al. |
| 5,803,906 A | 9/1998 | Pratt et al. |
| 5,842,976 A * | 12/1998 | Williamson ................. 600/300 |
| 5,883,370 A | 3/1999 | Walker et al. |
| 5,995,936 A * | 11/1999 | Brais et al. ..................... 704/275 |
| 6,157,036 A * | 12/2000 | Whiting et al. ......... 250/432 PD |
| 6,425,174 B1 | 7/2002 | Reich |
| 2001/0044755 A1 | 11/2001 | Sakamoto |
| 2001/0047281 A1 | 11/2001 | Keresman, III et al. |
| 2002/0010595 A1 | 1/2002 | Kapp |
| 2002/0017005 A1 | 2/2002 | Kim et al. |
| 2002/0093189 A1 | 7/2002 | Krupa |
| 2002/0155064 A1 | 10/2002 | Reubi |

(Continued)

OTHER PUBLICATIONS

United States Nuclear Regulatory Commision, NRC Regulations Title 10, Code of Federal Regulations. <http://www.nrc.gov/reading-rm/doc-collections/cfr/> Parts: 20,0, 32, 35, 39, and 60 (attached pp. 1-48).*

(Continued)

*Primary Examiner* — Sheetal R Rangrej
(74) *Attorney, Agent, or Firm* — Pillsbury Winthrop Shaw Pittman LLP

(57) ABSTRACT

An algorithm for generating of a program, as well as an associated method for handling of radioactive pharmaceuticals by a pharmacy so that data may be maintained on the acquisition, dispensing and handling of the radioactive pharmaceuticals and the disposition thereof. The algorithm and method allow for data to be electronically introduced in generally temporal relationship to the performance of physical activities. In addition, the algorithm and the method allow for computerized generation of required governmental reports, which thereby reduces the amount of manual operator attention which would otherwise be required. In addition, the algorithm and method allows for periodic information to be sent to quality control assurance personnel for generation of reports and information by such personnel.

15 Claims, 13 Drawing Sheets

U.S. PATENT DOCUMENTS

| | | | |
|---|---|---|---|
| 2002/0169636 A1 | 11/2002 | Eggers et al. | |
| 2003/0018495 A1 | 1/2003 | Sussman | |
| 2003/0033317 A1 | 2/2003 | Ziglin | |
| 2003/0105555 A1 | 6/2003 | Lunak et al. | |
| 2003/0131011 A1* | 7/2003 | Haunschild et al. | 707/100 |
| 2003/0204602 A1 | 10/2003 | Hudson et al. | |
| 2004/0078231 A1 | 4/2004 | Wilkes et al. | |

OTHER PUBLICATIONS

United States Nuclear Regulatory Commission, NRC Regulations Title 10, Code of Federal Regulations. <http://www.access.gpo.gov/cgi-bin/cfrassemble.cgi?title=200210>.*

United States Nuclear Regulatory Commission, NRC Regulations Title 10, Code of Federal Regulations. <http://www.access.gpo.gov/cgi-bin/cfrassemble.cgi?title=199910>.*

Petry, Neil A., "NRC and FDA Regulations Affecting Nuclear Pharmacy Practice", Journal of Pharmacy Practice, vol. II, No. 5 Oct. 1989; pp. 306-313.

Code of Federal Regulations. Nuclear Regulatory Commission (Parts 20 and 35) pp. 1-25 . <http://www.access.gpo.gov/cgi_bin/cfrassemble.cgi?title=200010>.

Nuclear Pharmacy Compounding Practice Committee, et al. Nuclear Pharmacy Guidelines for the Compounding of Radiopharmaceuticals. Jul. 17, 2001, pp. 1-31.

James A. Ponto and Joseph C. Hung. Nuclear Pharmacy, Part II: Nuclear Pharmacy Practice Today. Journal of Nuclear Medicine Technology; Jun. 2000; 28(2).pp. 76-84.

Code of Federal Regulations. Nuclear Regulatory Commission (Parts 20 and 35) 26 pages. http://www.access.gpo.gov/cgi_bin/cfrassemble.cgi?title=200010.

Code of Federal Regulations. Nuclear Regulatory Commission (Parts 20 and 71), http://www.access.gpo.gov/cgi_bin/cfrassemble.cgi?title=200010, 51 pages.

Code of Federal Regulations. Nuclear Regulatory Commission (Parts 20, 32, 36, 39 and 60) 38 pages. http://www.access.gpo.gov/cgi_bin/cfrassemble.cgi?title=200010.

Journal of Nuclear Medicine Technology, Nuclear Pharmacy, Part II: Nuclear Pharmacy Practice Today, James A. Ponto and Joseph C. Hung, Jun. 2000, 28(2), pp. 76-84.

Journal of Pharmacy Practice, NRC and FDA Regulations Affecting Nuclear Pharmacy Practice, Neil A. Petry, vol. II, No. 5, Oct. 1989, pp. 306-313.

Nuclear Pharmacy Compounding Practice Committee, et al. Nuclear Pharmacy Guidelines for the Compounding of Radiopharmaceuticals, Jul. 17, 2001, pp. 1-31.

* cited by examiner

| Products | |
|---|---|
| Code # | Product |
| 001 | Myoview |
| 002 | Myoview |
| | |
| | |
| | |
| | |

| Inventory | | |
|---|---|---|
| Code # | Amount | Eadiation |
| 001 | 50 ml | 5 mCi |
| 002 | | |
| 003 | | |
| 004 | | |
| 005 | 78 ml | 12 mCi |

| Scheduler | |
|---|---|
| Code # | Name |
| 012 | Smith |
| | |
| | |
| | |
| | |

| Elution | | |
|---|---|---|
| Code # | Amount (Radiation) | |
| 013 | 20 mCi | |
| | | |
| | | |
| | | |
| | | |

| Scheduler | |
|---|---|
| Code # | Name |
| 022 | Good Health |
| | |
| | |
| | |
| | |

| Accumulate Data | | | | | | |
|---|---|---|---|---|---|---|
| Code# | Product | Inventory Amount | Scheduler | Elution | User | Inventory Radiation |
| 002 | Myoview | | | | | |
| 001 | | 50ml | | | | |
| 010 | | | Smith | | | |
| 013 | | | | 21mCi | | |
| 022 | | | | | Fred Health | 5 Metric |
| | | | | | | |

FIG. 13

PHARMACY BASED METHOD AND ALGORITHM FOR HANDLING OF RADIOACTIVE PHARMACEUTICALS AND GENERATING OF REPORTS THEREFROM

RELATED APPLICATIONS

This application is based on and claims priority from our U.S. Provisional Patent Application Ser. No. 60/384,501, filed May 29, 2002, entitled Integrated Vertical Distribution System, Process and Algorithm For Providing And Distributing Radioactive Pharmaceuticals and Generating of Reports Therefor, and is also continuation-in-part of our U.S. Utility patent application Ser. No. 10/283,480 filed Oct. 29, 2002 now U.S. Pat. No. 7,630,907, entitled Algorithm and Program for the Handling and Administration of Radioactive Pharmaceuticals which claimed the benefit of and priority from U.S. Provisional Patent Application Ser. No. 60/335,088, filed Oct. 30, 2001, entitled Method Enabling Algorithm For the Handling And Administration of Radioactive Pharmaceuticals, the benefit and priority of which is also claimed by the instant application.

BACKGROUND OF THE INVENTION

1. Field of the Invention

This invention relates in general to certain new and useful improvements in algorithm and methods for enabling the preparation, handling and delivery of radioactive pharmaceuticals by a radioactive pharmaceutical supplier to a user, and more particularly, to an algorithm, and a software program used therein, and an associated method which allows for the production of radioactive pharmaceuticals and control over these pharmaceuticals and the areas in which they are used and for a system and method for maintaining records and generating reports, relating to the handling and the delivery of such radioactive pharmaceuticals.

2. Brief Description of Related Art

In recent years, the field of nuclear medicine has relied more heavily upon the use of radioactive pharmaceuticals, primarily for diagnostic purposes, but for other purposes, such as treatment purposes, as well. Generally, radioactive pharmaceuticals are introduced into a patient's blood stream, and allowed to be carried to one or more organs of the body which are to be examined. In this way, it is possible to specifically locate tumors or other dysfunction causing conditions.

Also, in the recent past, it has been found that certain tumors, and other dysfunction causing conditions, will not become visually apparent from presently available diagnosing techniques, such as magnetic resonance imaging and computer tomography. However, it has been found that these conditions will become visually apparent when radioactive dies are lodged or introduced into the tumors and other tissue in which observation may be necessary. Due to the greater widespread use of radioactive pharmaceuticals, and the potential for radioactive hazard, both in the handling and in the disposition of waste materials, there has been a need for careful control over the use of such materials. In fact, in the United States, both the federal government and the various state governments have levied numerous regulations controlling the use and disposition of these radioactive materials.

Inasmuch as the pharmacies are essentially the suppliers of the radioactive pharmaceuticals they are inherently in a position to provide data regarding the actual use and, to some extent, the disposition of these radioactive pharmaceuticals. Hence, the various governmental agencies responsible for the control of radioactive pharmaceuticals rely upon this data and are demanding of fairly accurate data regarding these radioactive pharmaceuticals.

It can be understood that there are numerous details involved in the handling and the use of radioactive materials and for that matter in the handling of these materials. As a result, the reporting requirements can be and frequently are extensive and involve the preparation of time consuming, labor intensive, and hence expensive reports. Not only have the users and pharmacies become involved in these myriads of reporting requirements, but the pharmacies themselves have had to report ever increasing amounts of information to the various governmental agencies. Hence, many pharmacies have had to hire full time personnel to do nothing more than generate reports.

The pharmaceutical houses which dispense these radioactive materials, are required to account for complete use of the radioactive materials, including the handling of the waste resulting therefrom. These pharmaceutical houses are also required to generate reports to those government agencies which are involved in the regulation thereof. The same holds true, to some extent, for the end users of these radioactive pharmaceuticals, as for example, the hospitals and the physicians and medical centers which are involved in the administration of these radioactive pharmaceuticals.

The pharmacies are typically involved in the business of acquiring or producing a pharmaceutical product and then imparting the desired amount of radiation to that product. They do not provide medical care or administer radioactive pharmaceuticals and do not keep data regarding the administration. However, the pharmacies are required to generate governmental reports which becomes a very time consuming and, therefore, an expensive task.

This increasing widespread use of radioactive pharmaceutical materials has given rise to a number of radioactive pharmaceutical supply facilities which supply the end users, e.g., medical institutions, hospitals and physicians with these radioactive materials. These organizations which primarily deal only in the generation and distribution of radioactive pharmaceuticals, are referred to as "pharmacies." Therefore, as used here, the term "pharmacy" shall mean and refer to only those organizations who deal in the generation and distribution of radioactive pharmaceuticals and who are or may be subject to governmental control in the production and/or distribution of such radioactive pharmaceuticals.

Initially, some of the pharmacies, and for that matter, even the end users, such as hospitals, etc., were originally quite lax in control of the radioactive materials, and in the maintenance of data for generation of reports. Consequently, the U.S. government and the various state governments, have enacted, and even tightened, regulations which require very accurate reporting on a periodic basis.

There have been attempts to use data processing techniques for storage of information. However, and heretofore, these data processing techniques generally rely upon the pure storage of information, without much attention being given to segregation of data for report preparation and auditing, and even for information purposes by the user thereof.

There has been, at least, a few attempts to provide a software program for these pharmacies to be used in the gathering of data and generating reports for the handling and delivery of radioactive materials. However, these attempts were somewhat rudimentary and did not take into consideration all of the numerous reporting requirements by the governmental agencies involved. Even more frequently, they did not have means for calculating data to be presented and hence, the user of the program had to necessarily do calculations by hand or through another program and then introduce that data into the particular software program for generating a report. In addition to the foregoing, the few software programs developed for pharmacies were not capable of universal use and did not take into consideration a large number of potential pharmaceutical materials which could be used and a variety of other conditions relevant to radioactive pharmaceuticals. In generally all cases, the software programs were lacking and required a substantial amount of personnel time in manually gathering information in order to generate the necessary reports.

One of the primary problems with the prior art software programs which have been generated for handling and delivery of radioactive materials by a pharmacy, is the fact that they were not particularly user-friendly. The operator of the system had to be fairly well experienced in dealing with computers in general, and in switching back and forth between subroutines in complex algorithms. As a simple example, if there were a menu page presented on the screen of a monitor, the operator would have to track the particular page involved, in order to examine details of a routine on that menu page. In many cases, the operator even had to go to additional menu screens in order to find the routine which was needed. Moreover, when the operator finished with one routine, the algorithm did not allow the operator to immediately return to the main screen, with a mere click of a pushbutton switch.

Another one of the problems inherent in the prior art systems is that they were not readily adaptable to changing requirements. Thus, if a governmental agency required a new type of report or an altered report to be generated, this almost necessitated the need for a skilled programmer to input that instruction base necessary for an operator to use. Consequently, the prior art programs were severely lacking in many respects.

There has therefore been a need for a system which will allow for the automatic retention of data, segregation of data according to specific functions and materials, and which will also generate reports based on the collected data, all on an automated basis. There has also been a need for systems of this type which could be universally applicable to the collection and segregation of data and generation of reports, based on the activities employed and the functions which are necessary by a pharmacy using such system.

In addition to the foregoing, there has been a need for these pharmacies to maintain internal controls over the use and dispensing of radioactive pharmaceuticals, in order to insure for the health and the safety of those users to whom they deliver these pharmaceuticals. This need for control over the radioactive pharmaceuticals also involves an intended need for careful control and monitoring of the areas in which the pharmaceuticals are used, inasmuch as these areas can also become contaminated from the radioactive pharmaceuticals.

Furthermore, there has also been a need for an orderly and regulated manner in which a radioactive pharmaceutical company could maintain appropriate record keeping in order to insure the delivery of radioactive pharmaceuticals which may be ordered. It may be appreciated that in many cases, the pharmaceutical activity of a radioactive pharmaceutical can decrease rapidly, depending upon the half life of the radioactive material. Consequently, careful control over the preparation of the radioactive materials and delivery must also be maintained.

3. Related Subject Matter

In my co-pending U.S. Utility patent application Ser. No. 10/283,480, filed Oct. 29, 2002, there is provided a method and algorithm for handling radioactive pharmaceuticals and which was designed for use by the ultimate user of the radioactive materials. Those users included for example clinics, hospitals, physicians and the like, who had need to use the radioactive pharmaceuticals with patients. That method and algorithm in the aforesaid copending application allows for the maintenance of records and acquisition of data relating to the use of the radioactive materials.

The data which is gathered can be used by the user, such as the clinic, etc. to govern its operations and to monitor quality control. The algorithm and method will allow for organization of the data so that such evaluation and monitoring can readily take place. That aforesaid algorithm and method also enables the generation to required governmental reports without substantial manual attention. There has been a need for an algorithm and a method for use by a pharmaceutical organization or so-called "pharmacy" to maintain similar data and generate reports therefrom. This present invention thereby provides an algorithm and a method which are suitable for use by a pharmacy.

OBJECTS OF THE INVENTION

It is, therefore, one of the primary objects of the present invention to provide an algorithm and a program, adapted for use with a pharmacy, dealing with materials irradiated with radioactive isotopes, capable of performing method steps used in a process for gathering data on such radioactive materials, and generating reports therefrom.

It is another object of the present invention to provide an algorithm and program of the type stated, which can be universally adapted to a variety of situations and a variety of radioactive materials which may be used.

It is a further object of the present invention to provide an algorithm and a program, for a pharmacy providing radioactive pharmaceuticals, which will automatically gather data, segregate the data according to specific materials and equipments used and the parties receiving such materials, as well as disposal thereof.

It is an additional object of the present invention to provide an algorithm and a program of the type stated, for a pharmacy providing radioactive pharmaceuticals, which can be fully automated and where reports can be generated with very little manual attention on a periodic basis, and containing that information precisely categorized and specified as required by various governmental agencies.

It is another salient object of the present invention to provide a method, for a pharmacy providing radioactive pharmaceuticals, to enable the gathering of data regarding the inventory and use of radioactive materials, and segregating that data according to report categories and allowing for generation of reports on a fully automated basis.

It is still another object of the present invention to provide a method of using an algorithm and a program, by a pharmacy providing radioactive pharmaceuticals, to efficiently, and with a minimal amount of manual intervention, permit the gathering of data arising from the use of pharmaceutical materials.

It is also an object of the present invention to provide a method and algorithm for use by a pharmacy providing radioactive pharmaceuticals, which will use data generated regarding the preparation, delivery and disposal of radioactive materials, and which will allow for generation of reports specific to the needs of various governmental agencies, and which reporting requirements can be altered in response to changing regulations of the various governmental agencies therefor.

With the above and other objects in view, our invention resides in the novel features of form, construction, arrangement and combination of steps involved in the algorithm and program as well as the method accomplished thereby in accordance with the present invention.

BRIEF SUMMARY OF THE INVENTION

The present invention primarily relates to an algorithm and a method and the software which can be generated from that algorithm for use in acquiring and distributing radioactive pharmaceuticals by a pharmacy and also collecting the necessary data in connection therewith. The algorithm and method of the invention is highly effective for use with a pharmacy or otherwise another supplier of radioactive pharmaceutical materials. In my copending U.S. patent application Ser. No. 10/283,480, filed Oct. 29, 2002 entitled Algorithm and Program for Handling Administration of Radioactive Materials, there is provided a complex algorithm and method generated by that algorithm which is effective for users, such as hospitals, clinics, physician's offices and the like, and which are hereinafter referred to as "patient facilities". There is a need for an algorithm which is effective for use with a pharmacy.

As indicated previously, the algorithm of this application and the algorithm of the aforesaid copending application are effective in that they allow for the gathering of data, and the segregating of that data which allows the generation of reports to various governmental agencies. It must be emphasized that due to the nature of the materials which are being produced, namely radioactive materials, the areas in which the radioactive pharmaceuticals are employed can become contaminated, the implements used in the producing or handling of the radioactive materials can become contaminated and the personnel who are handling this radioactive material equally can become contaminated. Moreover, due to the serious nature of the radioactivity and the fact that mere contact or proximity can contaminate an individual or other implement or location, very strict controls are employed. As a result, a great deal of data must be furnished to various governmental agencies and hence there is a need for an algorithm not only for the user, but for the pharmacy as well.

As indicated, the algorithm of the present invention and the software based on this algorithm are used in the generation of a method for the handling of radioactive materials and the implements used therewith. The algorithm of the invention allows for strict location control, as well, in that at each step of an operation, one who has need to know of the status of that radioactive pharmaceutical or the components used to produce that pharmaceutical will be able to easily access such information. Moreover, and due to the fact that these governmental agencies have strict requirements for reporting, the algorithm is highly detailed with regard to "quality control", as hereinafter defined.

In a very broad aspect, the algorithm first starts with those steps necessary for initial quality control, that is, quality control on the equipment used and the instruments used in handling the radioactive pharmaceutical, or the radioactive material, which may be used for irradiating a base pharmaceutical compound. All of the items which come into contact with the radioactivity and particularly the radioactive pharmaceuticals are referred to herein as "instrumentalities" or "implements". This terminology would include, for example, the items used in generation of the radioactive pharmaceuticals, at least to the extent that those items come into contact with radioactivity, and this would include work areas including countertops and the like which could become contaminated with the radioactivity.

Therefore, the term "implement" or the term "instrumentalities", as used in connection with the radioactive pharmaceutical, is used in a broad sense, in that it refers to a container for the pharmaceutical, a means for injecting the pharmaceutical, a means for disposing of the pharmaceutical and the like. The term implement also refers to surface areas on which the radioactive pharmaceutical may have been place or stored. In short the term "implement" refers to any item which may have received and been contaminated by radiation other than the radioactive pharmaceutical. Again, data is required to be maintained on all of theses items and areas and for that matter the personnel who deal with these radioactive pharmaceuticals. The term "quality control" is therefore used in this broad sense to refer to all of the activities of monitoring and maintaining data with regard to the radioactive pharmaceuticals and the implements used therewith.

As indicated above, in the algorithm there is a requirement for quality control. While quality control may be initiated at the beginning of any procedure, various quality controls are required throughout the procedure, largely due to the fact that radioactive pharmaceuticals are involved.

Following the initial quality control steps, the algorithm provides for the processing of an order. Typically, this order is referred to as a prescription and is submitted to the pharmacy by one or more authorized individuals who are authorized to receive radioactive pharmaceuticals.

After the order is processed, a determination is made at the pharmacy as to whether or not the radioactive pharmaceutical which is sought is in bulk quantity. If the radioactive pharmaceutical is in bulk form, then it is extracted from the bulk quantity and introduced into either a syringe or a container for the holding of the radioactive pharmaceutical. In this case, it must also be recognized that all of the implements which have been in the proximity of the radioactivity are, themselves, subject to being contaminated with the radioactivity and they may also contain radioactivity. When a product is deemed to exist in bulk quantity, both the pharmaceutical must be present in bulk form and that pharmaceutical must contain the desired dose of radioactivity. Thus, if the product sought by a patient facility or other user does not meet both criteria, then the pharmaceutical is deemed not to be in bulk form.

If the radioactive pharmaceutical is not available in bulk form, then the algorithm provides for the elution process. Although the elution process is more complicated than described herein, the elution process generally refers to producing the actual pharmaceutical compound which may have no radioactivity at that point, or otherwise acquiring that pharmaceutical compound. In any event, once the pharmaceutical compound has been made available, it is then eluted, that is it is exposed to a source of radioactivity until the desired dose of radioactivity has been irradiated into the pharmaceutical and at which point it becomes a radioactive pharmaceutical.

It should be recognized that at these important steps in producing or otherwise acquiring the radioactive pharmaceuticals that numerous quality control procedures are required. Moreover, data must be collected at each of these quality control procedures inasmuch as the reports to the governmental agencies will require the use of this data and moreover, in certain cases, data must be presented to the governmental agencies as well. Finally, periodic reports must be generated, as described above. Frequently, these reports are made on a daily basis to conform to many governmental requirements. Nevertheless, the reports must be submitted on a timely basis and the reports must be accurate. The algorithm of the invention allows for the generation of accurate reports and also timely reports. In addition, the algorithm allows for almost all automatic preparation of the reports. One of the unique facets of the algorithm is that it can be modified pursuant to changing governmental regulations. Thus, the algorithm of the invention is generally always current.

Another important facet to the radioactive pharmaceutical supplier, such as the pharmacy, is that of disposal. This term is used to refer to those activities the radioactive pharmaceutical itself and the implements used in connection therewith after the pharmaceutical has been administered. Again it must be recognized that the various implements used, both in the production of the radioactive pharmaceutical and in the administration of the radioactive pharmaceutical, as well as even in the return of the implements to the pharmacy. Again, since each of these implements and the remaining radioactive pharmaceutical still may contain a fair amount of radiation, they obviously cannot be disposed of by mere depositing with non-radioactive waste.

In many cases, thee user, such as the patient facility, will return syringes, beakers, bottles or the like which have become contaminated with the radioactive pharmaceutical to the pharmacy itself for disposition. Other methods for disposal of these radioactive pharmaceuticals and implements can also be employed but under strict government control.

In any event, the governmental agencies usually require strict control over the disposal of the radioactive pharmaceuticals. Since remaining portion of the radioactive pharmaceuticals and the implements can be contaminated, and their half-lives may extend over days, weeks or months, if not years, then control over these items must be maintained until the half-life has approached zero. Thus, disposal is a key factor in the activity of the pharmacy and is indicated requires data for generation of reports.

One of the important facets of the algorithm is the fact that many companies must have the assistance of and data input from a health physicist who is a type of quality control individual or organization. In order to complete reports for these governmental agencies, the health physicist may similarly be required to provide input data. The algorithm can allow for data from a health physicist if required. However, usually health physicist data would be coupled with the data provided by the user.

Inasmuch as the average pharmacy dealing with radioactive pharmaceuticals will provide such pharmaceuticals to a large number of users, and inasmuch as each user will administer these pharmaceuticals to a large number of patients, a substantial amount of data must be maintained. In addition, if there is a standing order for a particular patient, the pharmacy must know of the exact dates of the administration in the future for preparation of the radioactive pharmaceutical and automatic delivery. Thus, if a radioactive pharmaceutical is to be administered to a patient every third day, for therapeutic purposes, the pharmacy must be automatically alerted to produce that pharmaceutical in advance and have that pharmaceutical delivered to the user while allowing for decay time so that the pharmaceutical will still have the desired radioactivity when administered.

The algorithm of the invention is designed to receive input data not only about the users, such as the patient facilities, but about the particular patients and the pharmaceuticals which are to be administered. Moreover, all of this data must be organized in a reasonable fashion so that it can be accessed for generation of reports. The algorithm of the invention allows for presentation of information on a screen of a monitor at the pharmacy so that orders can be filled and delivered on a timely basis. Moreover, this includes standing orders which are periodic, as described above, as well as new orders. Moreover, the algorithm will be designed to present other information such as the doses, including the dose of the actual pharmaceutical and the dose of the radioactivity. In this way, the pharmacy can prepare the pharmaceuticals for delivery on a timely basis.

In addition to the foregoing, the algorithm allows for setting the dates and times, and continuously updates the date and time, relative to the information which has been stored. The algorithm of the invention also allows for necessary attendant operations, such as billing for preparation and providing of the radioactive pharmaceutical, the maintaining of insurance information, and the like. The input data will include input data regarding the physician, the type of pharmaceutical which has been prescribed, and like information.

One of the important aspects of the present invention is that personnel are not required to operate calculators in order to make determinations. In effect, all computations which are necessary in connection with the administration and the record keeping, are performed internally with the algorithm and programs. As a simple example, by introducing the weight of a patient, the amount of the radioactive pharmaceutical to be administered to that patient can be determined.

In substance, it is not necessary for the user to engage in the need for locating a calculator, looking up a formula to enable calculation, and thereafter, performing the necessary calculation. This alone not only functions as a time conservation, but it also eliminates the possibility of error in performing the calculation function. In addition, the algorithm of the present invention will also provide for ranges to inform the operator as to whether or not a particular calculation was high or low. As a simple example, if an operator is performing a daily constancy determination, that is, e.g., meters operating in accordance with the recommended ranges, the algorithm will give the previous ranges, both high and low, so that the operator can automatically determine right at that point in time if the meters are within the corrected range or not within the corrected range.

The algorithm and the program derived therefrom can also be customized to the needs of a particular pharmacy. This is due to the fact that the algorithm is arranged to maintain data in various data groups, and combine that data to produce information which must be presented to an operator of the system. Moreover, by virtue of the fact that the computer itself can be connected to the World Wide Web, or other global communication network, it is possible to update and download and upload information on an on-line basis.

One of the important aspects of the present invention is the fact that the algorithm and the method allow for the automatic assignment of internal numbers to various segments of data. As a simple example, if the radioactivity pharmaceutical Myoview is to be delivered to a patient facility by the name of XYZ, and in an amount of 50 ml., each of those pieces of information are assigned an internal computer number. Thereafter, each of the pieces of information are stored in a separate file. In this way, it is not necessary to introduce redundant data for another user who is to be delivered Myoview, in the same or different amounts. The algorithm thereupon allows for the assumption of data through the internal computer numbers, as requested by the operator. Indeed, it is not even necessary for the operator to know of these internal numbers. Rather, the internal numbers represent an internal file accessing scheme for the gathering of data and associating the data.

Another one of the important aspects of the present invention relies on the fact that the algorithm has been designed so that it is essentially "fool proof", in that an operator who may be relatively unskilled in computer operations can, nevertheless, perform all of the necessary method steps with the method generating algorithm of the present invention. The algorithm is designed to generate one or more main displays in the form of flow diagrams on the screen of a computer monitor. Each of the routines forming part of that algorithm are laid out in a manner in which they must be sequentially performed.

In view of the fact that there is a complex amount of information and a complex number of tasks to address, the menus are designed so that each of the routines are not only in their proper sequential location on the screen in which they are to be performed, but the operator can immediately address any particular routine merely by the click of a return push-button switch on the keyboard pad of the computer. Moreover, after the operator has performed all of the tasks necessary in a particular routine, another mere actuation of the return switch, or other selected switch, will cause the program to return to the main screen so that the operator immediately knows the next routine which is to be performed.

Even when a routine is performed, the operator can automatically and easily address subroutines by simple actuation of another keyboard switch. In this way, the algorithm effectively carries the operator through all of the routines which must be performed, thereby avoiding problems of faulty memory or problems which involve a lack of computer skills on the part of the operator. When the operator has finished with a subroutine, the click of the same switch will automatically bring the operator back to the routine, and another click of the return switch will automatically bring the operator to the main menu. In this way, the algorithm is so designed so that there is little chance for error.

The various routines are also organized so that the operation is relatively simplified. As a simple example, the scheduling of delivery of radioactive pharmaceuticals to a particular user is contained in one routine, the preparation of a pharmaceutical for a patient in another routine, determination of delivery times in a third routine, selection of a mode to dispose of implements in a fourth routine, etc. The routine even provides for introduction of the initials of the operator so that one can track the efficiency of use of the operator.

The algorithm and the method accomplished thereby, is hereinafter described in more detail in the following detailed description. However, certain individual activities are not necessarily included therein. For example, a selection of a desired word processor which may be incorporated in the program is not necessarily described, and the type of forms which may be stored and selected are not necessarily described. In addition, activities such as backup recording, help files, and the like, may be included with the algorithm, but since these activities are not critical to the operation of the method, they are neither illustrated nor described herein.

This present invention thereby provides a unique and novel algorithm and associated program and the method steps taken through the use of the algorithm and program for fulfilling steps in the acquisition, handling and delivery of radioactive pharmaceuticals, which thereby fulfills all of the above-identified objects and other objects which will become more fully apparent from the consideration of the forms in which it may be embodied. One of these forms is more fully illustrated in the accompanying drawings and described in the following detailed description of the invention. However, it should be understood that the accompanying drawings and this detailed description are set forth only for purposes of illustrating the general principles of the invention.

BRIEF DESCRIPTION OF THE DRAWINGS

Figure 1:
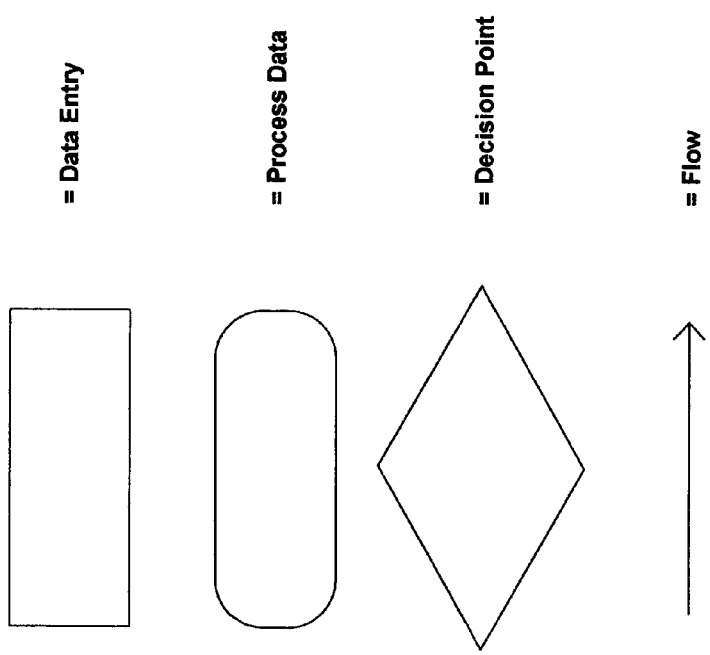
Figure 2:
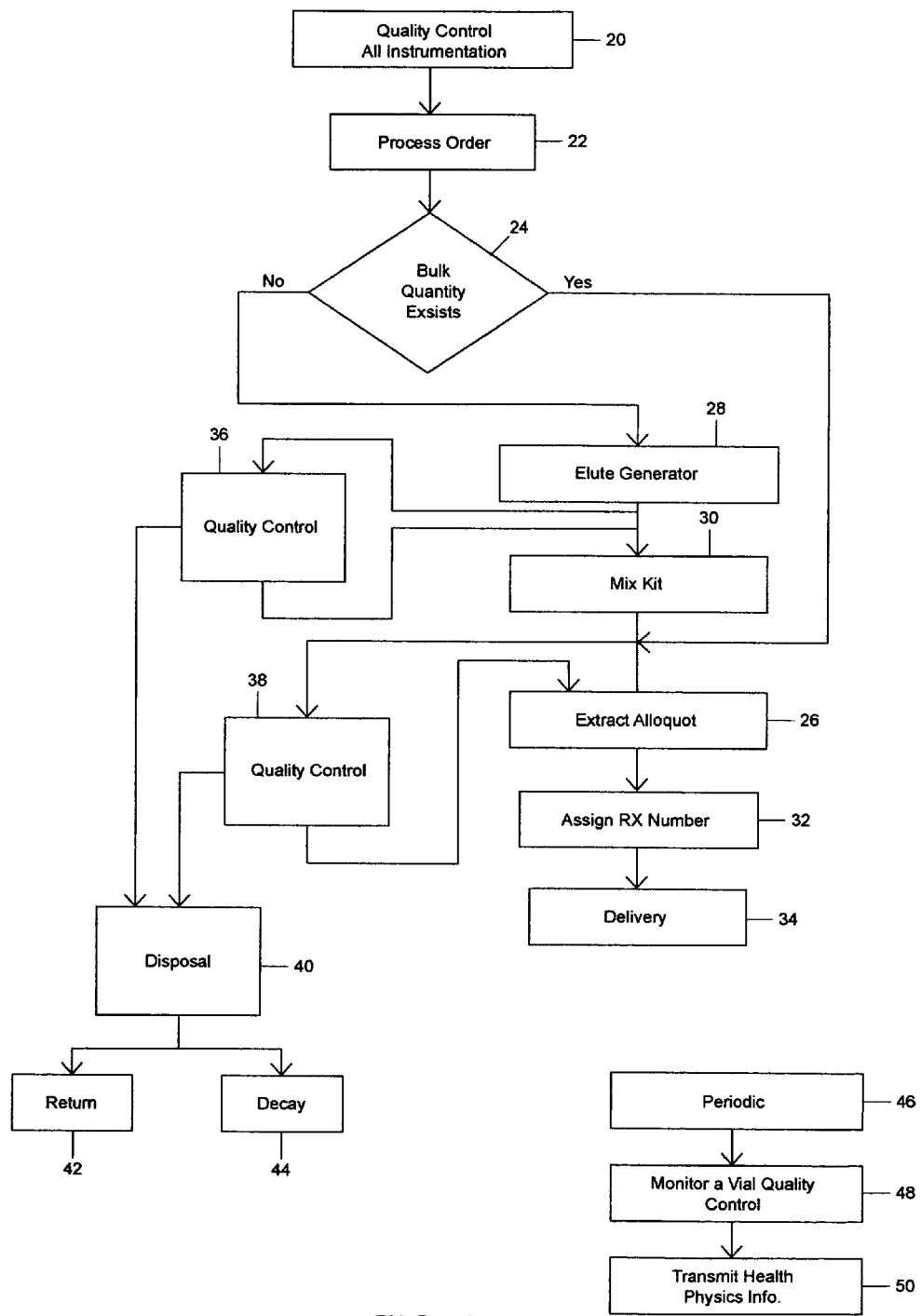
Figure 3:
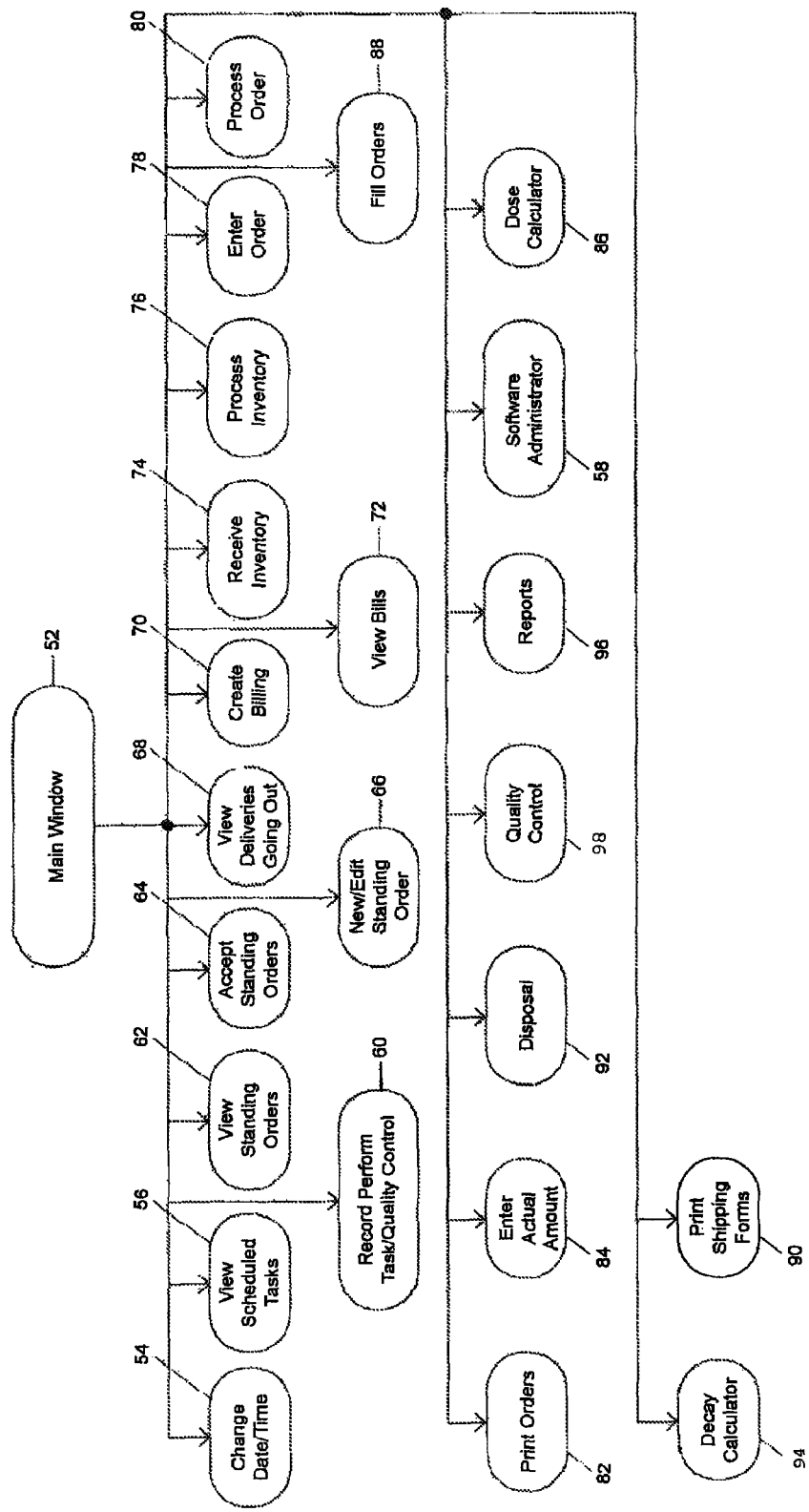
Figure 4:
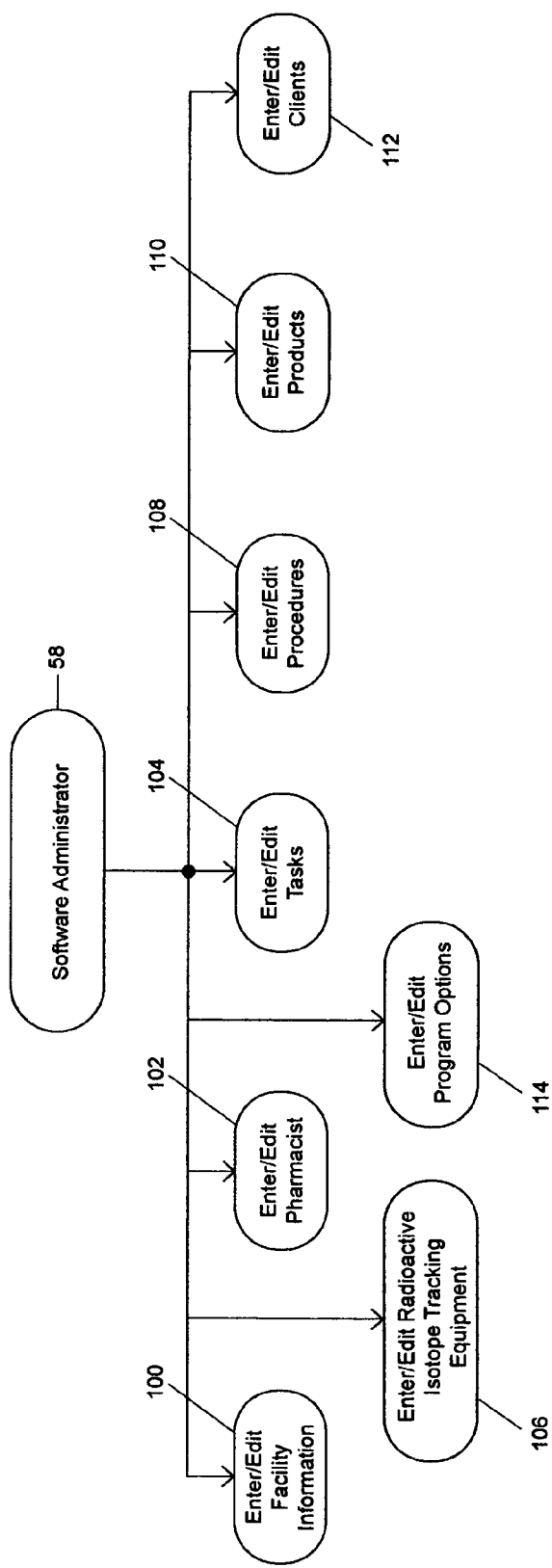
Figure 5:
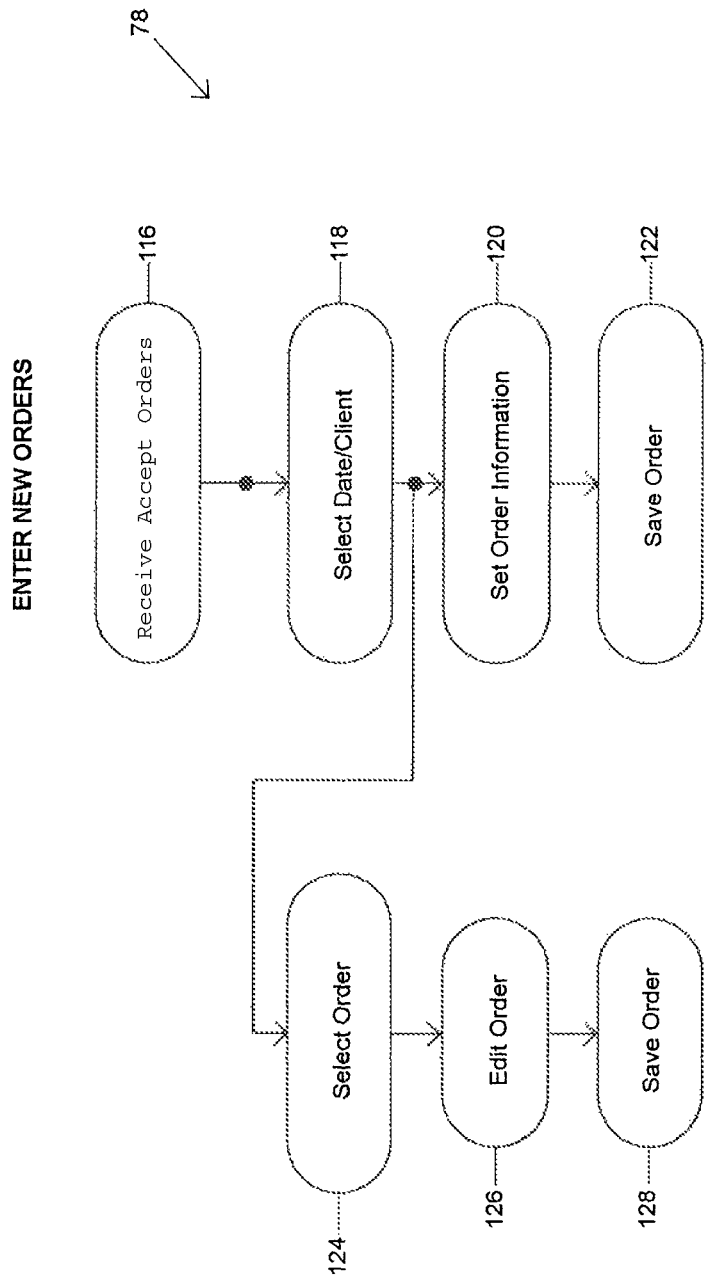
Figure 6:
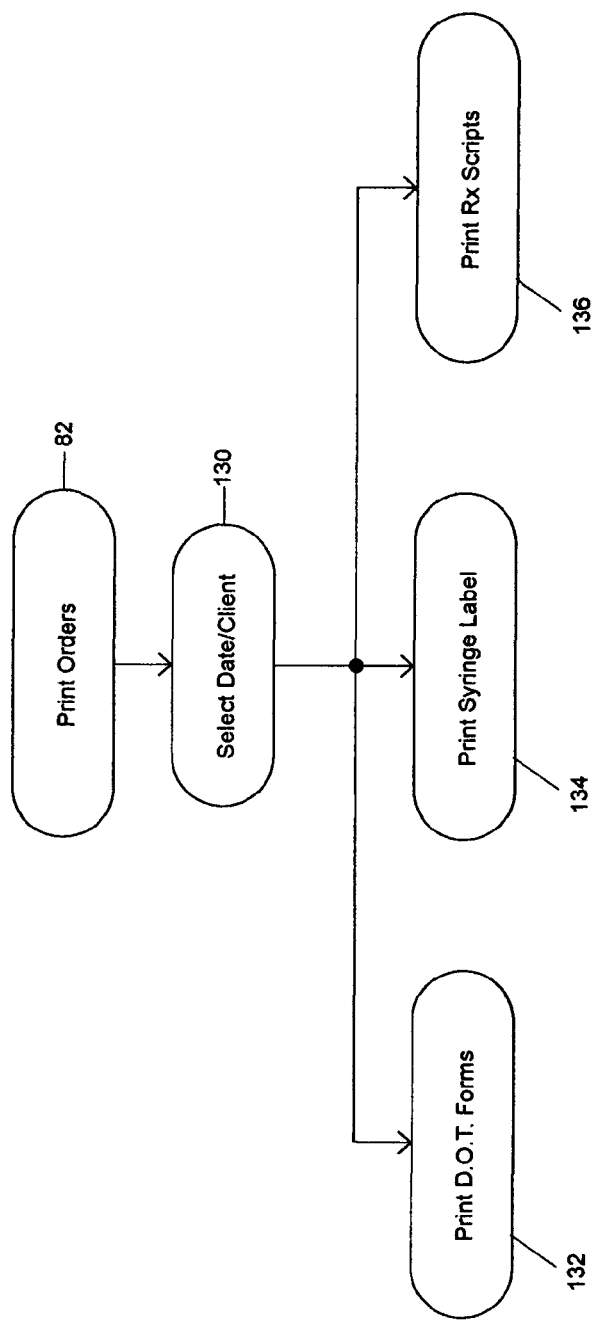
Figure 7:
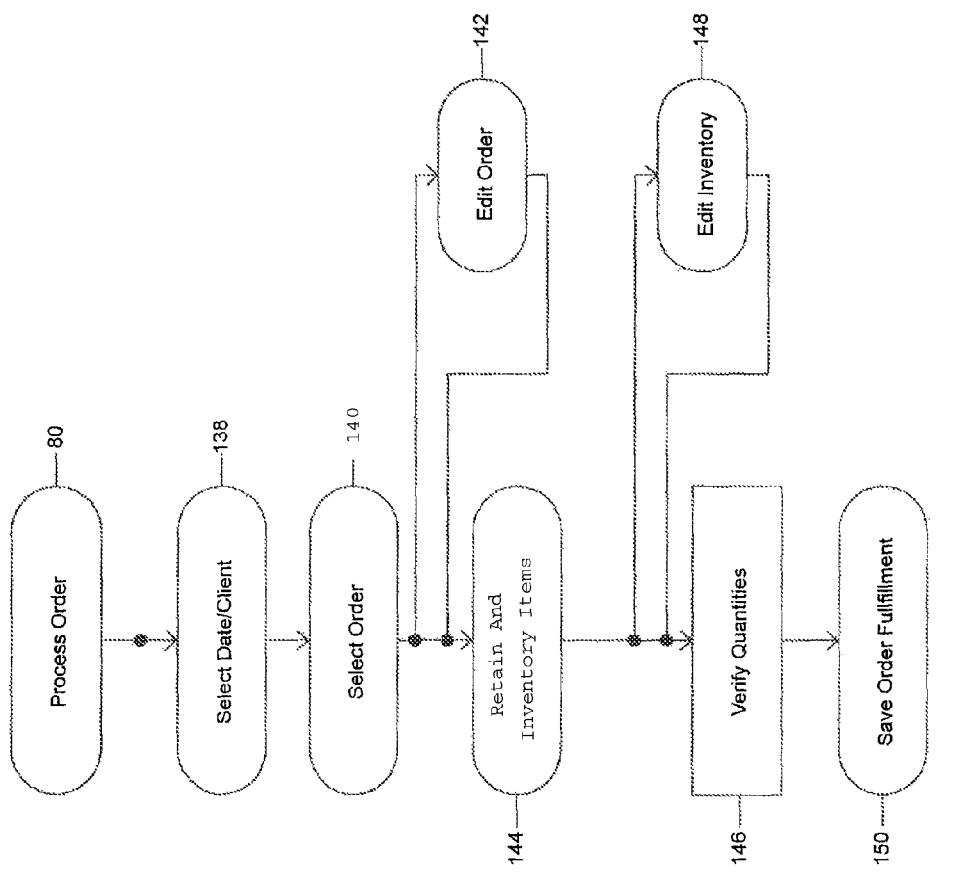
Figure 8:
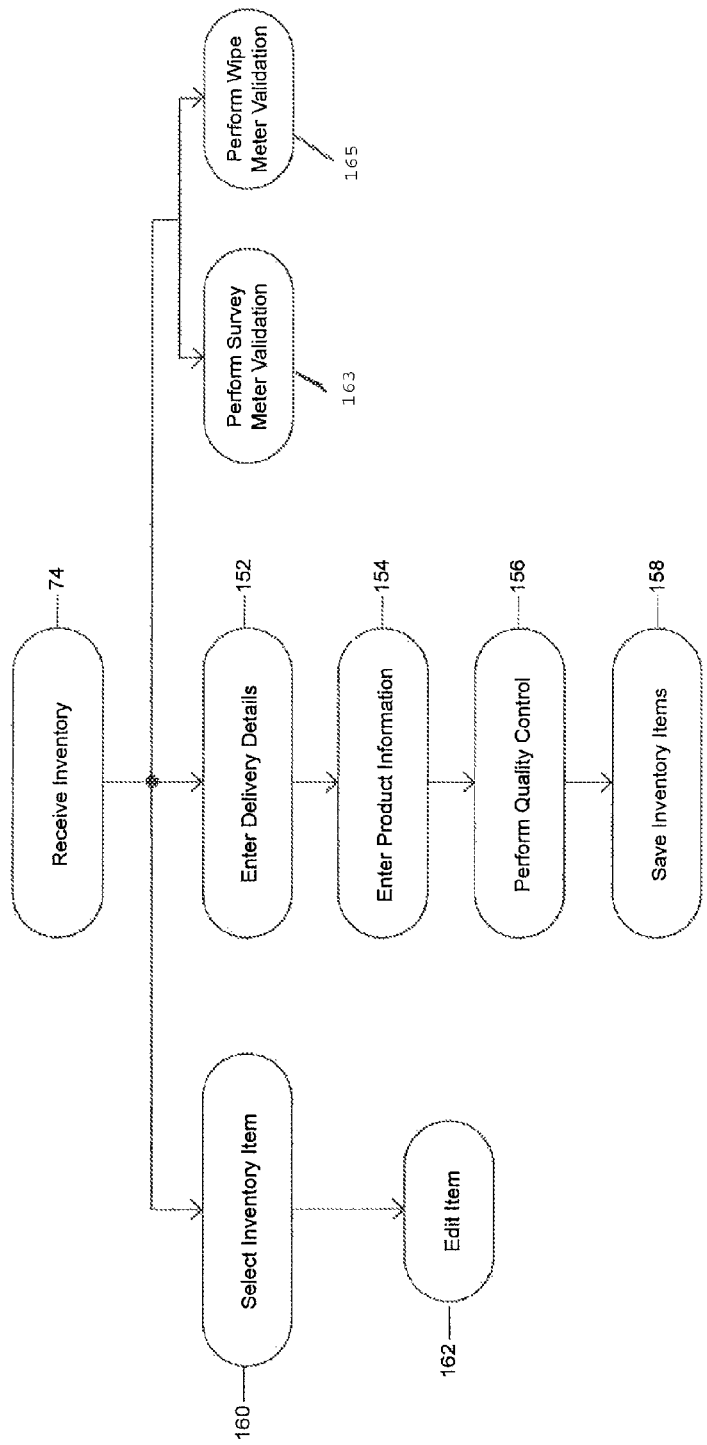
Figure 9:
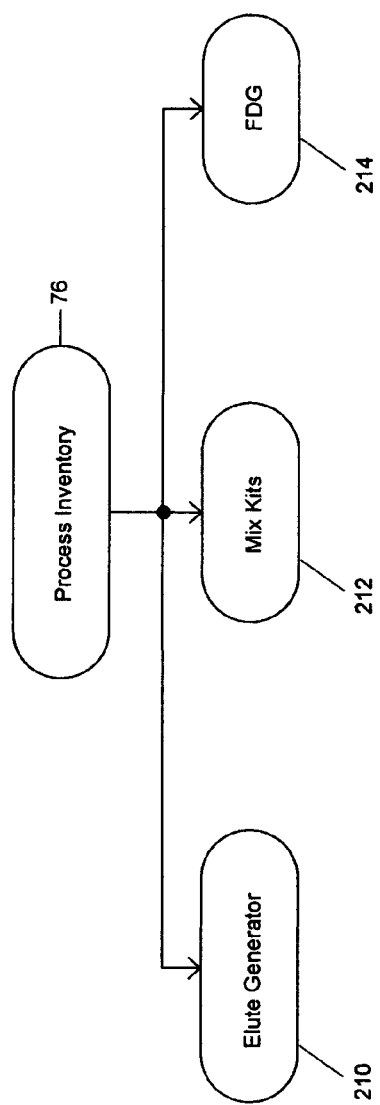
Figure 10:
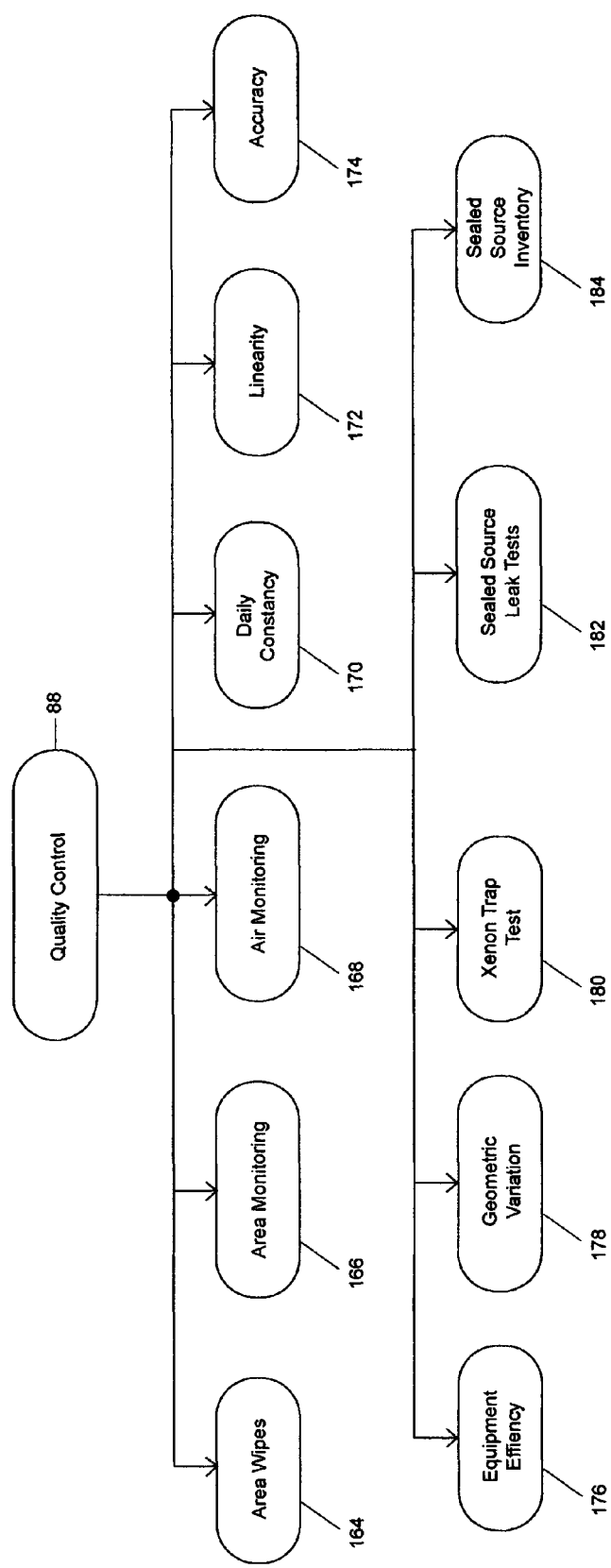
Figure 11:
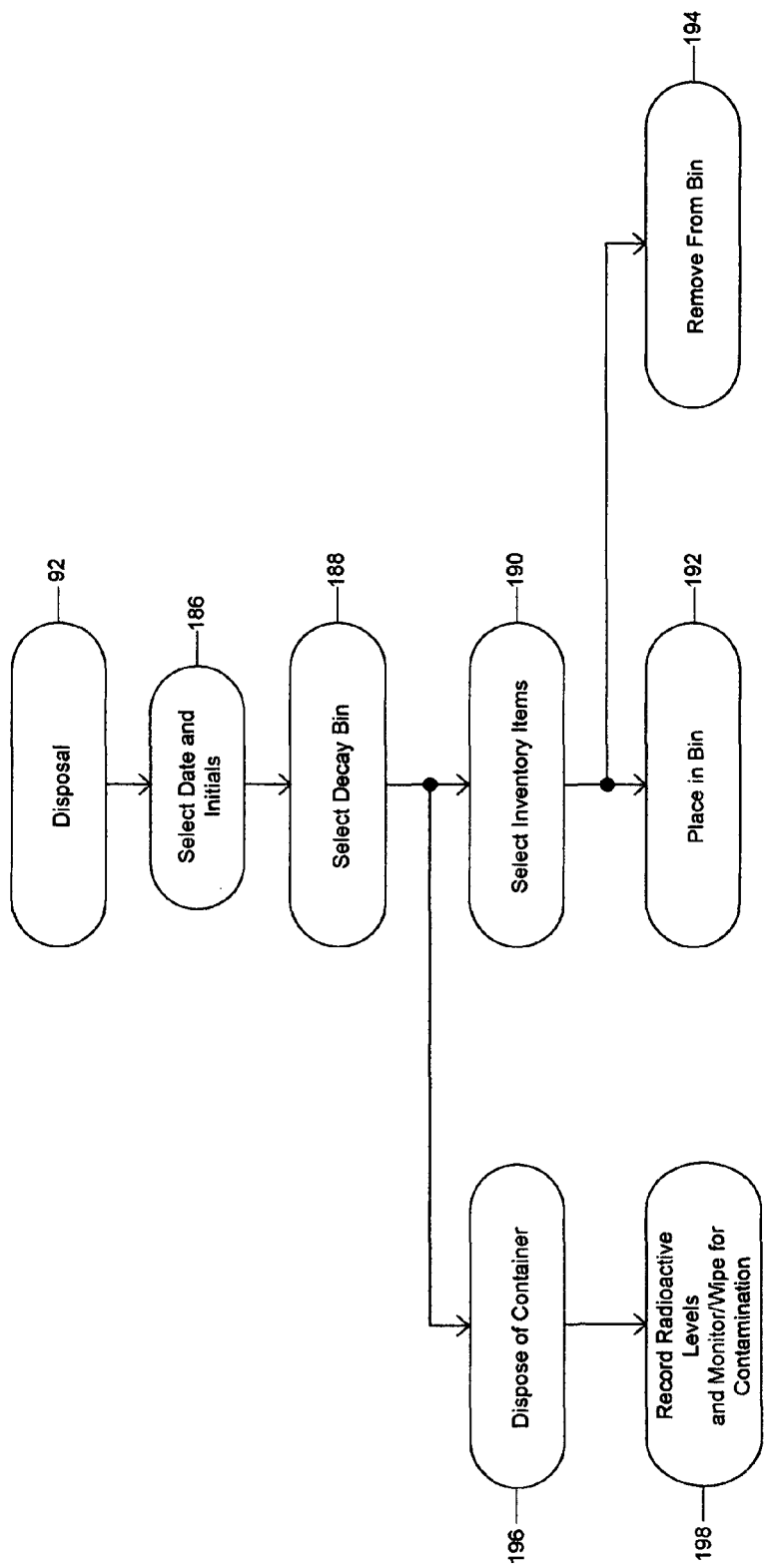
Figure 12:
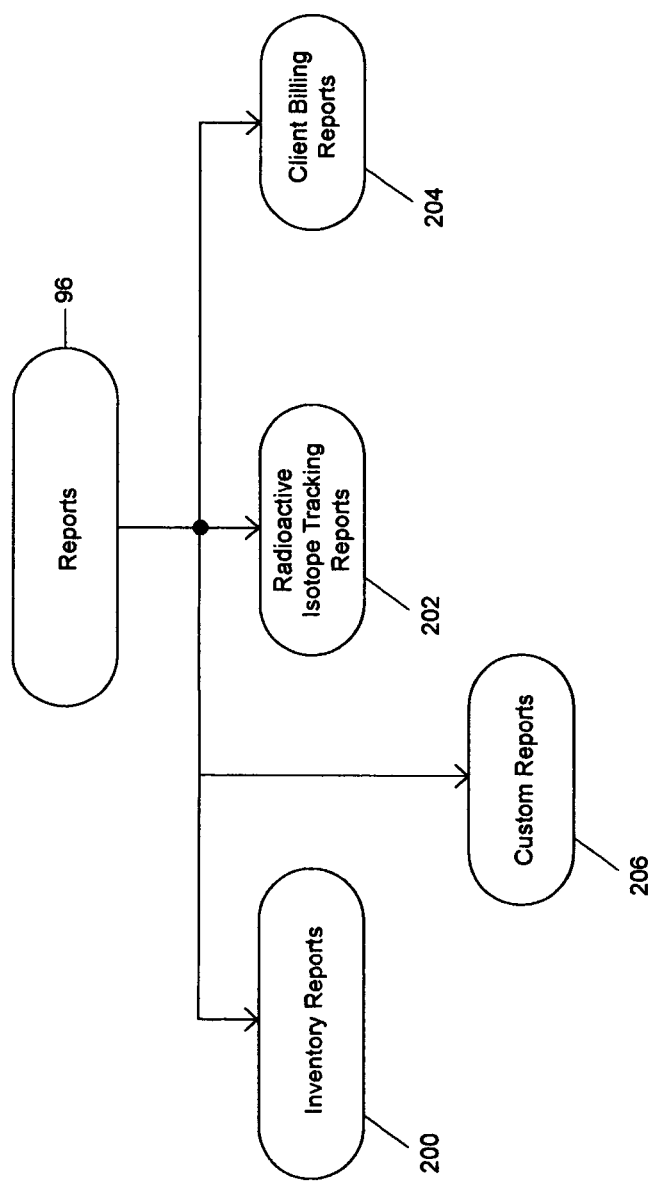

Having thus described the invention in general terms, reference will now be made to the accompanying drawings (13 sheets) in which:

FIG. 1 is a symbol identification of the various symbols used in the following schematic block diagram flow sheets, forming part of the algorithm and method of the present invention;

FIG. 2 is a schematic block diagram flow sheet, showing the main steps forming part of a broad generic algorithm and method of the present invention;

FIG. 3 is a schematic block diagram flow sheet, showing the main routines involved in the algorithm of the invention;

FIG. 4 is a schematic block flow diagram, showing the steps involved in the software administration routine of the algorithm which generates displays of activities to be performed;

FIG. 5 is a schematic block flow diagram chart showing those steps involved in the entering order routine in accordance with algorithm of the present invention;

FIG. 6 is a schematic flow diagram, showing the routine for printing orders, in accordance with the algorithm and method of the present invention;

FIG. 7 is a schematic flow diagram, showing the steps involved in the routine for processing of orders, in accordance with the algorithm and method of the present invention;

FIG. 8 is a schematic flow diagram, showing the steps involved in the routine for receiving of inventory for the algorithm and the method of the present invention;

FIG. 9 is a schematic flow diagram, showing the routine for processing of inventory in the algorithm and method of the present invention;

FIG. 10 is a schematic flow diagram, showing the quality control routine for radioactive pharmaceutical material and implements contaminated thereby in the algorithm and method of the present invention;

FIG. 11 is a schematic flow diagram, showing the steps involved in the routine for disposal in the algorithm and method of the invention;

FIG. 12 is a schematic flow diagram, showing the steps involved in the generation of a report in accordance with the present invention; and FIG. 13 is a schematic block diagram showing the fields in which data is introduced, and in the preparation of a radioactive pharmaceutical for a particular patient facility.

DETAILED DESCRIPTION OF A PREFERRED EMBODIMENT

The algorithm of the present invention is more fully described by reference to the following FIGS. 1-13. It should be recognized that this particular algorithm and method are primarily adapted for use with a radioactive pharmaceutical supplier, e.g. a pharmacy or other facility authorized to acquire and deliver radioactive pharmaceuticals.

FIG. 1 illustrates the symbology which is used, and to that extent, is self explanatory with regard to data entry and processing of data, as well as a decision point. The decision point typically has more than one output, such that if a decision is "yes", for example, then one output occurs, and if a decision is "no", then another output occurs. In the actual algorithm, one can automatically move to a selected routine or subroutine, illustrated on these various figures.

Each of the following routines are identified with a description of each routine. To a large extent, many of the steps are self explanatory, and do not require further explanation.

Referring now to FIG. 2 of the drawings, there is set forth a generalized overall view of the algorithm for use with a pharmacy dealing with nuclear medicine and particularly radioactive pharmaceuticals, as well as the implements used in connection therewith. FIG. 2 illustrates as a first step, 20, an initial quality control in all areas and all instruments. This is accomplished in order to determine if the area of the facility in which the radioactive pharmaceutical is being used or prepared is in a clean state, and also to determine any present level of radioactivity so that an increase can also be determined. Thereafter, the pharmacy based algorithm will allow for the processing of an order at step 22. In particular, this step includes a large number of steps as hereinafter described, and which actually call for the presenting of the order on the screen of a monitor and the delivery of the order.

The order is filled using either of two major techniques. The first of these techniques comprises the withdrawal from a bulk quantity. Therefore the algorithm provides for a decision at step 24 which determines whether or not the radioactive pharmaceutical exists in bulk quantity. This implies not only in terms of volume content, for example, but also radioactivity content as well. If the ordered pharmaceutical does exist in bulk quantity, then an adequate amount is extracted at step 26. If it does not exist in bulk quantity, then the second technique relies upon an elution technique and therefore the pharmaceutical is eluted in an elution generator at step 28. In this step, the raw pharmaceutical is then irradiated with the desired amount of radiation. Thereafter, a mix kit is formed at step 30. This effectively implies that the pharmaceutical may be eluted or otherwise provided in a kit form to a user such as a patient facility. Again, after the elution process, an aliquot amount is extracted at step 26 and the remainder held in bulk storage. After a desired amount of the pharmaceutical has been extracted, there is an assignment of a prescription number at step 32 and this is followed by a physical delivery at step 34. Each of these steps, as well as the preceding steps, require the maintenance of data for generation of reports and the like.

Two of the major activities involved in producing a radioactive pharmaceutical are quality control and disposal, as aforesaid. Therefore, it can be observed that a first quality control step is performed at step 36, after a raw pharmaceutical is eluted in an elution generator. The same procedure occurs at step 38, if the radioactive pharmaceutical meets quality control and if the pharmaceuticals thus produced meet quality control standards, then the adequate amount is extracted at step 26. If the produced radioactive pharmaceutical does not meet the quality control standards then the disposal routine is employed at step 40. Several government approved techniques can be used for disposal of the radioactive pharmaceutical and for that matter the implements used in connection therewith. As indicated previously, these implements will include, for example, syringes, vials, mixers and other elements which may have come into contact with or have been in proximity to the radioactivity for a time sufficient for themselves to become radioactive. Two of the major techniques used for disposal is that of return to another facility at step 42, or otherwise storage, and decay at step 44, until the half life of the radioactivity has reached a point close to zero.

Also associated with the algorithm of FIG. 2 are steps involving the use of a health physicist. Many governmental reports require separate independent data from a health physicist. In this case, the health physicist will also use periodic procedures at step 46 and which is followed by monitoring of the quality control at step 48. As indicated previously, since quality control, as defined herein, is such an important facet, oftentimes independent evaluation by a health physicist is required. Thereafter, the health physicist will transmit a health physicist's report at step 50 which can be combined with, or the data therefrom used with, a report provided by the pharmacy or by the end user or both.

As indicated previously, FIG. 2 sets forth a broad algorithm for operation in the method of the present invention. FIG. 3 more fully illustrates the overall main flow diagram showing the various steps involved in the algorithm of the invention. Some of these steps are actual routines which are described more fully in detail in the following FIGS. 4-12.

Returning now to FIG. 3, there is provided a main display 52. The main display 52 will essentially provide a snapshot or image or picture of the various routines which are used in handling of the radioactive pharmaceuticals by the pharmacy. These various routines are not presented in any particular order in FIG. 3 since all of the routines are necessary in the preparation of a radioactive pharmaceutical and delivery of this pharmaceutical as well as the record keeping for generation of reports.

At the outset, before the algorithm is actually used, it is necessary for the operator to insert the date and time or to change the date and time, appropriately, as may be required at step 54. The setting of the date and time is important inasmuch as the radioactive pharmaceuticals may have a rapid decay time and the required pharmaceutical must be prepared recognizing that there will be a decay in the delivery to the patient facility and in the actual administration to the patient. Hence, timing in the preparation and delivery is an important factor.

The various tasks for the day or other period may be viewed at a scheduled task routine 56. The actual tasks are scheduled and introduced into the computer at a software administrator routine 58. In this case, an operator would set up the various tasks for that day or for that other period such as a week, for example, at step 58.

There is also a separate routine 60 for recording tasks as provided. Usually, the tasks which are performed at this routine are quality control tasks. There is, for example, a quality control lookup so that there is, in effect, a menu informing an operator of the various quality control tasks which must be performed for any particular operation involving a radioactive pharmaceutical.

At this point in the process, the operator is then able to view standing orders at routine 62. These orders may have been orders previously introduced into the processing system for disposition at the time of viewing. For example, there may be a standing order for certain radioactive pharmaceuticals to be delivered to a certain patient facility. In like manner, the computer may be operated to have these orders reviewed periodically. At that point, the operator then determines whether or not to accept the standing order at routine 64. At this point, the process is adapted to examine new orders which may have been sent since the last examination of the display at step 66.

At this point, the operator can then view the schedule of deliveries at step 68. There is little activity from an electronic data processing standpoint at step 68. The user of the system may also wish to record the making of a delivery after the physical delivery has been made.

Billing is an important facet in any algorithm and there is provided a billing routine 70. In this case, the billing routine provides for the creating of the billing. This would also include the sending of the billing. Moreover, the billing routine would include those activities such as follow-up and preparation of additional bills if the initial bill is not paid. Bills may also be viewed at step 72 as shown in FIG. 3. At this point, the operator may then turn to the status of inventory. Inventory received can be electronically recorded at step 74. Moreover, the inventory may be processed at routine 76. In effect, at step 76 dealing with the processing of the inventory, certain components would be received and used in the production of another component of pharmaceutical. Thus as a simple example, if a base non-radioactive pharmaceutical is received at step 74, it can be processed by eluting the same at step 76 in order to produce a radioactive pharmaceutical. For this purpose, the radioactive pharmaceutical is deemed to be a different product than the base non-radioactive pharmaceutical which was delivered.

Orders which were viewed can then be entered and processed. The orders are entered at 78 and processed at 80. When an order is entered, a determination is made as to whether or not the order can also be accepted. If the order does not appear to be an authorized order or one going to a known source, then it may not be processed. Otherwise, processing of the order may take place at step 80. The orders may be printed at step 82. In actuality, after an order is entered, it is probably printed before the order is processed, that is the order is filled.

In connection with the filling of an order, it is necessary to specify the amounts both of the actual non-radiated pharmaceutical and also the level of radioactivity which may have been eluted into that pharmaceutical and this is accomplished at step 84. In addition, in order to prepare an order, and in some cases, the party making the order and who desires to receive the radioactive pharmaceutical may not know the actual amount of radioactivity which is to be eluted to that pharmaceutical in order to make the same a radioactive pharmaceutical. Moreover, a determination must be made as to the amount of radioactivity depending upon the condition of the patient who is to receive that radioactive pharmaceutical, that is, such as age, sex, health condition and the like. This is accomplished at a dose calculator routine 86.

Although a physician may prescribe a selected amount of a non-radioactive pharmaceutical base, the pharmacy is frequently in a better position to determine the amount of radiation which should be imparted. This is accomplished in connection with the dose calculator routine 86.

There is actually provided a fill order routine 88. In this respect, the entering of orders routine 78, the processing order routine 80 and the printing order routine 82 and to some extent even the dose calculator routine 86 would all be subroutines with respect to the fill order routine 88.

As indicated previously, the order may be filled either by removal of an adequate portion from a bulk storage as indicated in connection with FIG. 2, or otherwise, it may be eluted to contain the desired amount of radiation.

At this point, the radioactive pharmaceutical is essentially ready to be packaged for delivery. The radioactive pharmaceutical may be contained within a vial or other container or it may be literally packaged in a syringe form. In any event, and in that regard, the container itself will become irradiated and also become a source of radiation which may contaminate other areas. Consequently, that vial or other container of radioactive pharmaceutical would have to be properly packaged for delivery to a user such as a patient facility. The algorithm is thereafter adapted to print the necessary shipping forms for delivery of the radioactive pharmaceutical at step 90. Actually, the printing of the shipping forms constitutes a delivery routine and this could be expanded so as to record information about the delivery, if required.

As indicated previously, disposal of any remaining radioactive pharmaceutical and the implements contaminated thereby must then occur. For this purpose, there is provided a disposal routine 92. There are several government approved techniques which can be used for disposal of the remaining radioactive pharmaceutical and the implements used therewith. Hopefully, the type of radioactivity which is eluted to a pharmaceutical base has a sufficiently high decay rate such that storage of the radioactive pharmaceutical is not unduly long. However, as indicated previously, the half life must be at least sufficiently long so that the amount of radioactivity needed for either the therapy or testing purpose is not depleted prior to the use thereof by the user. In this respect, since the implement or the remaining radioactive pharmaceutical must be retained until there is almost zero radioactivity level remaining, the half life is preferably relatively short. In any event, the pharmaceutical must be retained while there is any substantial amount of radioactivity remaining and the same holds true for the implements used therewith.

In this respect, governmental agencies are usually interested in the necessary data with regard to disposal of the pharmaceuticals and the implements used therewith. Consequently, a substantial amount of data must be maintained with respect to both the pharmaceutical and the implements. Specifically, data such as whether the implements and remaining pharmaceutical were shipped to another location or to an authorized disposal source or if it is being retained for decay, must be identified. The algorithm of the invention is designed to retain all of this data and segregate the data for generation of reports as hereinafter described.

The disposal routine is also effective as a record keeping mechanism for determining where to hold items for decay. If an item had been irradiated with uranium, for example, having a relatively long half life, any implement having a half life equivalent to that of other items in the storage box would be included in that box. Otherwise, if the isotope was a more rapidly decaying isotope, the implement or the pharmaceutical would be stored with those other items having the relatively shorter half life. In this way, it is possible for the pharmacy to maintain a plurality of lead boxes in which the remaining radioactive pharmaceuticals and the implements contaminated thereby are stored. The data therefor can be kept in this disposal subroutine 92.

Closely associated with the disposal routine 92 is the decay calculator routine 94. In this routine, there is provided programming for using the starting date and the ending date of a particular radioactive isotope. The routine can then calculate the amount of radioactivity remaining as of the given end date. The routine is adaptable for recalculating by changing the ending date, as may be desired. This is an important facet in connection with the present invention, inasmuch as it is not necessary for an operator to sit with a calculator and tables in order to calculate the remaining radioactivity. The algorithm of the invention is adapted to calculate the remaining radioactivity and that remaining radioactivity is automatically used in connection with the disposal routine 92.

There is also provided a separate report routine 96. As indicated previously, reports must be periodically prepared not only for internal use, but for use with various governmental agencies. Failure to timely file such reports, or for that matter failure to accurately provide such reports can result in substantial sanctions. Consequently, it is important to insure both timely and accurate reporting. Moreover, the reporting of the end user, or pharmacy, must be essentially consistent with that provided by the health physicist. The data which is accumulated by entry of the data during the entire process starting from the viewing of an order to the delivery of the prescription for that order requires numerous elements of data to be inserted. That data is automatically segregated into the various data tables described in connection with FIG. 13. When so segregated, the data can then be automatically and easily accessed for generation of the desired reports in the routine 96.

There is also provided a quality control routine 98. The quality control routine actually constitutes several quality control steps which are conducted throughout the performance of the algorithm. As a simple example, quality control is conducted initially each day before any orders are filled and quality control is conducted after certain procedures and even at the end of the day. A substantial amount of quality control data is therefore obtained and this quality control data is again segregated and used in the reports at routine 96.

Typically, in the quality control, area monitoring is conducted, a hot labs routine is conducted and the like. These activities are more fully described in the aforesaid copending utility patent application for use by users. Consequently, it is not necessary in connection with the present invention to describe the details of these various activities in connection with quality control. It is sufficient to note that the procedures employed are frequently established by various governmental agencies and therefore those procedures are conducted so that the necessary data can be obtained for the generation of the reports at routine 96.

It should be recognized that other routines could be added to the main overall display 52. However, they are not absolutely necessary in connection with the operation of the algorithm. As a simple example, there could be provided a routine which actually allows for access to a word processing program or a routine for separate calculations or the like. There could actually be additional routines and for that matter additional subroutines in connection with those specified in the algorithm of the invention.

FIG. 4 illustrates a routine for software administration. As indicated previously, this is the routine for setting up certain tasks to be performed on a daily basis or other periodic basis. The software administrator routine 58 has a first subroutine for entering and editing information about a particular facility at step 100. Specifically, this subroutine could also provide other information with regard to the particular facility that may be of interest to the party who may be filling an order for a particular facility.

There is also provided a step 102 for entering the name or identification of persons dealing with the radioactive pharmaceuticals or the implements used in connection therewith. In this case, the name of a pharmacist, for example, and the name of a technician as well as other parties dealing with these items could also be entered at this point. In this way, it is possible to identify a source of data which may have been introduced into the database operated by the algorithm of the invention.

The routine 58 also allows for the entry or editing of tasks which were previously identified in connection with the software administrator routine 58. Thus, there is a separate step 104 for entry of these tasks or editing of same. There is also a step 106 for either entry of or editing of information regarding the radioactive isotope tracking equipment. More specifically this includes, for example, a survey meter or a wipe meter used in quality control procedures. In this step, information regarding the identification of the equipment and for that matter information regarding the readings of the equipment can be entered.

The software administrator will also provide for a step 108 allowing for the entry or editing of procedures which can be conducted. This may include, for example, certain medical procedures which are to be conducted at a particular day or other time interval. It may also include the steps which may be involved in connection with that medical procedure. Thus, if a scan is to be conducted on a patient on a certain date the entry into this particular step would constitute a reminder alerting the operator of the need for that scan. The algorithm also allows for entry of products at step 110. Thus, as a simple example, if Myoview was going to be used, it would be entered in the system and the name of that product and the identification of the product would be stored in one of the databases. Typically, inasmuch as the product is identified as a radioactive pharmaceutical, not only does the amount of the composition have to be identified, but the amount of the radioactivity may be identified. In actuality, the radioactivity could be identified and stored with the amount thereof stored in a different database than the quantity.

The routine of the software administrator 58 also allows for entry of or editing of clients of the pharmacy at step 112. This may also include, for example, certain physicians or even technicians at the client facility. The client facility may typically adopt the form of a patient facility as, for example, a hospital, clinic or the like.

The software administrator routine also includes an option entry or editing step 114. This step will allow the user to add other items to the software administrator or to modify items in the software administrator for reminder purposes. Thus, as a simple example, the user can enter a step to identify certain items which may be stored in a particular container. Moreover, this step would allow for entry of additional steps which would prompt the operator to determine information on the inside and the outside of a particular container. More specifically, this step would allow one to modify the program to conform to his or her particular needs.

FIG. 5 more fully illustrates several of the main steps involved in the enter order routine 78. As the initial step, orders are accepted or received at step 116. At step 118 the particular client that is, for example, the patient facility is selected as well as the date, product information and the like. Thereafter, the order information is set at step 120. The name of the party who ordered a particular radioactive pharmaceutical, the particular name of the pharmaceutical, the actual delivery time and date and related information is all introduced at this point in the process. The order is then saved at step 122. Also, after the particular client and data has been selected, the order itself is selected at step 124. In this case, a particular order out of several orders which may be present for that day is selected. Moreover, an order for a particular patient facility or other user is also selected at step 124. The order is edited at step 126 and saved at step 128.

The routine for printing orders 82 is more fully set forth in FIG. 6 of the drawings. In this case, in order to print an order, a particular client, such as a patient facility, is selected along with a date for that particular client at step 130. The orders can be printed at step 132 and labeling or other information can be prepared at step 134. For example, labels may be printed for the syringes and the like. These labels would contain the name of the radioactive pharmaceutical, the amount of radiation contained in the pharmaceutical, perhaps the name of the patient, the name of the physician and like information. A prescription label or the like can be printed at step 136.

The routine for processing an order 80 is more fully shown in FIG. 7 of the drawings. When an order is received, a determination is made in this routine as to whether or not the prescription constituting that order is in the inventory, that is it is in a bulk form. At this point, the particular client such as the patient facility is determined for processing of an order and the date is entered at step 138. Thereafter, the particular order is selected at step 140. In this step, the amount of radiation contained in the radioactive pharmaceutical, as for example, 5 millicuries, is determined. At this point, it is either possible to edit the order at step 142 or to provide for retention and inventory item at step 144. At this point, the routine moves to a step 146 for verifying quantities. If the quantity of the desired pharmaceutical is present, it can be withdrawn or the inventory can be edited at 148. An order can also be saved at step 150. At that same point, the order can also be filled. In step 150, if the order is to be combined from two different vials it is possible to determine which quantities can be mixed in order to constitute the required prescription.

The routine for receiving inventory 74 is more fully presented in FIG. 8 of the drawings. In this case, the delivery details for receiving of an order is entered at step 152. At that point, the delivery details would constitute such items as a container number, product in that container, delivery time, the manufacturer delivery number and other identifying information. The routine then moves to step 154 for entering product information. The name of the product is identified at step 154 and this would also include information regarding the amount of radiation in the product. Moreover, it would also include related information on the bottle such as the calibration date and the calibration time and other related data. The routine then provides for the performing of a quality control operation at step 156. In this case, the quality control is performed on a vial inside of the container. It may also be performed on both the inside and the outside of the outer container itself. The transportation information with regard to this container is also identified. From there, the routine will save the inventory item at step 158.

The routine also provides for selection of the inventory item essentially simultaneously with the entry of the delivery details. The selection of the inventory item occurs at step 160 and thereafter any editing of that inventory item can occur at step 162. This step 162 allows the operator to correct the information which was entered regarding the entry of a product information at step 154. Survey meter validation can be performed at step 163 and a wipe meter validation can be performed at step 165.

Processing of inventory constitutes the Routine 76 as shown in FIG. 9. This includes an elution of a pharmaceutical 210, which is followed by preparation of a mixing kit 212, which in turn is followed by FDG 214.

As indicated previously, quality control is conducted at various stages during the entire operation of preparing and filling orders for radioactive pharmaceuticals. Initially, a wipe meter test and area monitoring are conducted. The wipe meter test information is provided at step 164 and the area monitoring at step 166. Moreover, air monitoring is also conducted at step 168. In many cases, there is a requirement for monitoring the air in a facility to determine the amount of radioactivity in the air. In the area wipe test, the test actually involves the wiping of an area with a tissue and measuring the amount of radioactivity on the tissue. In the area monitoring, the entire area in which the radioactive pharmaceutical is prepared is monitored as for example, counters and the like.

Thereafter, a daily constancy test is conducted at step 170. The daily constancy information is that to determine whether or not the meters taking various readings are consistent. Thus, if the meters are consistent then the accuracy is correct. If the meters are not consistent, then they must be re-calibrated.

In addition, linearity tests are conducted at 172. In a linearity test an amount of radiation is determined with a specific quantity of a fluid in a vial. The amount of fluid in the vial is then increased by a certain percentage as, for example, a hundred percent. Nevertheless, the amount of radioactivity should be consistent, that is, the same. If not, then there is an error somewhere in the reading process. Linearity tests are conducted to be sure that the same instrument is providing the same readings over a span of time as, for example, two to three days. If an item with a known decay rate is measured, that item must have the same known amount of radiation which would be determined on the decay. By knowing the specific amount of radiation in an item it is possible to determine the linearity of a particular instrument. Accuracy measurements are also made at step 174.

Equipment efficiency is determined at step 176. Efficiency is conducted with a meter and probe. The material actually has only a finite degree of efficiency in giving off radiation. Therefore, we must determine the accuracy of the equipment in measuring that information and this is conducted at step 176. A geometric variation is conducted at step 178. In this case, a cylinder containing a radioactive source is dropped into a case. It is important to insure that the radiation amount is the same regardless of the variations in volume in that cylinder.

A xenon trap test is conducted at step 180. In this case, the amount of xenon in the air is trapped in a filter. As the air exits a room, it passes through the filter. At that point, the filter must be measured to determine the amount of xenon which may be passing from the room, when dealing with a radioactive xenon source.

A sealed source leak test is performed at step 182. In the sealed source leak test, a vial having a radioactive on the inside is wiped on the outside. In this way, it is possible to determine the amount of radioactive leakage occurring with that vial. A sealed source inventory is conducted at step 184. In this case, it is possible to account for radiation in a source and the amount of radiation which may be given off as, for example, the amount of radiation in a uranium source and the amount of radiation in a cobalt source. It is important to determine if the radiation from a container having a uranium or cobalt irradiated item is giving off that radiation.

The disposal routine 92 is more fully shown in FIG. 11 of the drawings. As indicated previously, disposal constituted numerous steps and numerous related requirements for record keeping for various governmental agencies. The disposal routine 92 is more fully illustrated in FIG. 11 of the drawings. Initially, the date and initials of an operator are introduced at step 186. Thereafter, the decay bin for a particular item is selected at step 188. As indicated previously, it is desirable to locate a waste item having a degree of remaining radiation in a container with other items having roughly the same half life time. In other words, an item would be inserted in a container having a half life no longer than any other item in that container.

After selection of the decay bin, the inventory items to be disposed are selected at step 190. For example, when the use of a syringe is finished, that syringe must be identified with respect to a particular bin. It is then placed in the bin at step 192. It can also be removed from a bin at step 194 and introduced into another bin.

Disposal of the container occurs at step 196. Again, after a particular decay bin has been selected, provision is made for disposal of the container. Radioactive levels are recorded at step 198. Also, a monitor wipe for contamination is conducted at step 198.

The reports routine 96 is more fully set forth in FIG. 12 of the drawings. In this case, inventory reports are prepared at step 200 and radioactive isotope tracking reports are prepared at step 202. The inventory reports are usually prepared for internal use. The radioactive isotope tracking reports are prepared largely for governmental purposes. Client billing reports are prepared at step 204. The algorithm allows for generation of custom reports at 206. In this case, the reports routine can be altered by a user at the user's discretion to generate any custom report desired by that user.

FIG. 13 illustrates the formation of data tables for use with a pharmacy in the algorithm about the present invention and which also shows a significant feature of the invention. In this case, data is broken down into segments so that there is not a redundancy in information recordation. When the operator introduces information, the data processing system, as for example, a computer, assigns a computer code number to each of the segments of the data. Those segments of the data can then be correlated. Thus, when the operator introduces information regarding a user, such as a patient facility, and the radioactive pharmaceutical which may be administered, pursuant to a prescription for a patient, and the amounts, the amounts may be categorized in one data table, the radioactive pharmaceutical in another data table and the name of the patient facility in a third data table.

If radioactivity information is to be introduced with respect to the pharmaceutical, that information may be introduced into a fourth table, etc. In this way, if the operator wishes to recall data for a given patient facility, the computer will automatically locate the internal computer numbers given to that patient facility's name and locate the radioactive pharmaceutical and the amount and the radioactivity of that pharmaceutical. In the case of another patient facility, the same radioactive pharmaceutical may be delivered to that other patient facility in perhaps different amounts. Consequently, the name of the radioactive pharmaceutical and other pieces of information are not duplicated in the data system.

As a simple example of the foregoing, if a particular radioactive pharmaceutical, Myocene, was introduce into the computer it might be arbitrary assigned a code of 001 and Myoview would be given an arbitrary code of 002. If it was desired to determine the amount of these compounds in the inventory of the facility, the operator can merely introduce the compound from 001 and determine that e.g., 50 mg was available in inventory. From another section of that data bank, it can be seen that the radioactivity is 5 millicuries. In addition, if the scheduler's name was required to be entered, it would not be necessary for the schedule to introduce that information again creating a redundancy, but rather the scheduler's name would be available under Code 010. The dose amounts may available in another table and other information is in other tables.

When it is desired to accumulate this data to determine, for example, the amount of a product in inventory for an order from a patient facility, that data may be present in the bottom chart of FIG. 13. Thus, in this case, the radioactive pharmaceutical Myocene with an inventory amount of 50 ml., is to be delivered to a patient facility by the name of Good Health, in a dose amount of 50 ml. The scheduler who arranged for that information is identified as Smith. Thus, all information is easily and quickly gathered and generated on a displayed screen without necessarily causing the operator to again introduce redundant information and without causing the need for storage of redundant information.

Another one of the important aspects of the present invention, as briefly described above, is the fact that a complete screen showing a routine, for example, may be presented on the monitor. In this way, the viewer can examine all subroutines which must be required, otherwise, the steps which must be performed. When the viewer then accesses any particular subroutine, the subroutine will automatically present those steps necessary for the operator to accomplish that subroutine. The operator performs those steps and upon execution of a return or other keyboard push button switch on the computer keyboard the algorithm will automatically return to the that subroutine or to the main menu.

If the operator forgets that a certain subroutine had been performed, that subroutine will immediately inform the operator that the activity has been performed on that particular day. Thus, the algorithm is essentially fool-proof in that it literally carries the operator through every step that must be performed and almost forces the operator to perform each such activity.

Thus, there has been illustrated and described a unique and novel pharmacy based method and algorithm and program for handling of radioactive pharmaceuticals and generating reports therefor and which thereby fulfills all of the objects and advantages which have been sought. It should be understood that many changes, modifications, variations, and other uses and applications which will become apparent to those skilled in the art after considering the specification and the accompanying drawings. Therefore, any and all such changes, modifications, variations, and other uses and applications, which do not depart from the spirit and scope of the invention are deemed to be covered by the invention.

Having thus described the invention, what we desire to claim and secure by Letters Patent is:

1. A computer-implemented method for introducing and processing of data related to ordering and distributing of radioactive pharmaceuticals, the computer-implemented method causing an electronic data processing system to:
   a) receive, at the electronic data processing system, an order for a radioactive pharmaceutical;
   b) examine a previously recorded database of the electronic data processing system to determine if a mix kit of the ordered radioactive pharmaceutical exists in inventory, wherein the mix kit is formed by exposing a pharmaceutical material to radiation;
   c) generate extraction instructions, at the electronic data processing system, to extract a dose of the ordered radioactive pharmaceutical from the mix kit of the ordered radioactive pharmaceutical if the mix kit is available, the extraction instructions including a volume and a radioactivity level for the dose;
   d) receive radioactive activity information for the extracted dose at the electronic data processing system, the radioactivity level being measured after the dose has been extracted;
   e) record the extracted dose information into the database of the electronic data processing system, the extracted dose information including a volume and radioactive activity level of the extracted dose;
   f) generate, by the electronic data processing system, a prescription number for the extracted dose of the radioactive pharmaceutical and record the prescription number in the database of the electronic data processing system; and
   g) generate, by the electronic data processing system, delivery instructions for the extracted dose of the radioactive pharmaceutical and record the delivery instructions in the database of the electronic data processing system.

2. The computer-implemented method for the introducing and processing of data related to the ordering and distributing of radioactive pharmaceuticals of claim 1, the computer-implemented causing an electronic data processing system to: receive, aliquot readings for the radioactive pharmaceutical, including volume and radioactivity level, before generating extraction instructions.

3. The computer-implemented method for the introducing and processing of data related to the ordering and distributing of radioactive pharmaceuticals of claim 1, the computer-implemented further causing an electronic data processing system to: receive patient health condition information and to calculate the volume and radioactivity level of the dose based on the patient health condition information, including calculating a desired radioactive activity level of the dose.

4. The computer-implemented method for the introducing and processing of data related to the ordering and distributing of radioactive pharmaceuticals of claim 1, the computer-implemented further causing an electronic data processing system to: receive a radioactive activity level for an implement used in the obtaining the extracted dose of the radioactive pharmaceutical, the implement radioactivity level being measured after the dose has been extracted and record the implement radioactive activity level and a time of measurement into the database of the electronic data processing system.

5. The computer-implemented method for the introducing and processing of data related to the ordering and distributing of radioactive pharmaceuticals of claim 4, the computer-implemented further causing an electronic data processing system to: generate disposal instructions for the implement used in obtaining the extracted dose of the radioactive pharmaceutical based on the received radioactive activity levels, the disposal instructions identifying a bin where the implement is stored to allow the radioactive activity levels to decrease before the implement is disposed.

6. The computer-implemented method for the introducing and processing of data related to the ordering and distributing of radioactive pharmaceuticals of claim 1, the computer-implemented further causing an electronic data processing system to: receive Wipe meter test information and store the wipe meter test information in the database of the electronic data processing system to verify an area where the dose was extracted has acceptable radioactivity levels.

7. The computer-implemented method for the introducing and processing of data related to the ordering and distributing of radioactive pharmaceuticals of claim 1, the computer-implemented further causing an electronic data processing system to generate instructions to print labels for the extracted dose of the radioactive pharmaceutical.

8. A computer-implemented method for introducing and processing of data related to ordering and dispensing of radioactive pharmaceuticals by a pharmacy, the computer-implemented method causing an electronic data processing system to:
   a) receive, at the electronic data processing system, an order for a radioactive pharmaceutical;
   b) examine, a previously recorded database of the electronic data processing system, to determine if a bulk quantity of the ordered radioactive pharmaceutical exists in inventory;
   c) generate, at the electronic data processing system, preparation instructions for creating a mix kit of the ordered radioactive pharmaceutical if the bulk quantity of the ordered radioactive pharmaceutical does not exist in inventory, the mix kit being created by exposing a pharmaceutical material to radiation;
   d) receive, at the electronic data processing system, a measured radioactivity level for the mix kit of the ordered radioactive pharmaceutical and recording the the measured radioactivity level for the mix kit in the database of the electronic data processing system;
   e) generate, at the electronic data processing system, extraction instructions to extract a dose of the ordered radioactive pharmaceutical from the mix kit, the extraction instructions including a dose volume and a dose radioactivity level;
   f) receive measured dose radioactivity levels for the extracted dose of the ordered radioactive pharmaceutical at the electronic data processing system to verify the measured radioactivity level corresponds to the dose radioactivity level specified in the extraction instructions;
   g) record the extracted dose information in the database of the electronic data processing system, the extracted dose information including the dose volume and the measured radioactivity level;
   h) generate, at the electronic data processing system, a prescription number of the extracted dose of the radioactive pharmaceutical at the electronic data processing system and record the prescription number in the database; and
   i) generate, at the electronic data processing system, delivery instructions for the extracted dose of the radioactive pharmaceutical and record the delivery instructions in the database.

9. The computer-implemented method for the introducing and processing of data related to the ordering and distributing of radioactive pharmaceuticals of claim 8, the computer-implemented method causing the data processing system to receive performing quality control procedures including: a) measuring radioactivity levels of an area after receiving the extracted dose information for the radioactive pharmaceutical and receiving wipe survey radioactivity levels after receiving the extracted dose information for the radioactive pharmaceutical to verify the area where the dose was extracted has acceptable radioactivity levels.

10. The computer-implemented method for the introducing and processing of data related to the ordering and distributing of radioactive pharmaceuticals of claim 8, the computer-implemented method causing the electronic data processing system to: receive aliquot readings for the radioactive pharmaceutical, including volume and radioactivity level, before generating extraction instructions.

11. The computer-implemented method for the introducing and processing of data related to the ordering and distributing of radioactive pharmaceuticals of claim 8, the computer-implemented further causing an electronic data processing system to: receive patient health condition information and to calculate the volume and radioactivity level of the dose based on the patient health condition information, including calculating a desired radioactive activity level of the dose.

12. The computer-implemented method for the introducing and processing of data related to the ordering and distributing of radioactive pharmaceuticals of claim 8, the computer-implemented further causing an electronic data processing system to: receive a radioactive activity level for an implement used in the obtaining the extracted dose of the radioactive pharmaceutical, the implement radioactivity level being measured after the dose has been extracted and record the implement radioactive activity level and a time of measurement into the database of the electronic data processing system.

13. The computer-implemented method for the introducing and processing of data related to the ordering and distributing of radioactive pharmaceuticals of claim 12, the computer-implemented further causing an electronic data processing system to: generate disposal storage instructions for the implement used in obtaining the extracted dose of the radioactive pharmaceutical based on the received radioactivity levels, the disposal instructions identifying a bin where the implement is stored to allow the radioactivity levels to decrease before the implement is disposed.

14. The computer-implemented method for the introducing and processing of data related to the ordering and distributing of radioactive pharmaceuticals of claim 8, the computer-implemented further causing an electronic data processing system to generate instructions to print labels for the extracted dose of the radioactive pharmaceutical.

15. The computer-implemented method for the introducing and processing of data related to the ordering and distributing of radioactive pharmaceuticals of claim 8, the computer-implemented further causing an electronic data processing system to: receive wipe meter test information and store the wipe meter test information in the database of the electronic data processing system to verify an area where the dose was extracted has acceptable radioactivity levels.

* * * * *